United States Patent
Wik

(10) Patent No.: US 7,925,339 B2
(45) Date of Patent: Apr. 12, 2011

(54) INTUBATION MONITORING APPARATUS AND METHOD

(75) Inventor: Lars Wik, Oslo (NO)

(73) Assignee: Medinnova AS, Oslo (NO)

( * ) Notice: Subject to any disclaimer, the term of this patent is extended or adjusted under 35 U.S.C. 154(b) by 1722 days.

(21) Appl. No.: 10/517,989

(22) PCT Filed: Jun. 19, 2003

(86) PCT No.: PCT/NO03/00208
§ 371 (c)(1),
(2), (4) Date: Jan. 25, 2005

(87) PCT Pub. No.: WO2004/004541
PCT Pub. Date: Jan. 15, 2004

(65) Prior Publication Data
US 2005/0256422 A1 Nov. 17, 2005

Related U.S. Application Data

(60) Provisional application No. 60/390,115, filed on Jun. 21, 2002.

(30) Foreign Application Priority Data

Jun. 19, 2002 (NO) .................................. 20022950

(51) Int. Cl.
A61B 5/05 (2006.01)
A61B 5/08 (2006.01)
(52) U.S. Cl. ....................... 600/547; 600/536
(58) Field of Classification Search ................ 600/506, 600/533, 536, 547; 128/200.26, 207.14–207.17, 128/899
See application file for complete search history.

(56) References Cited

U.S. PATENT DOCUMENTS

| 4,403,215 | A | | 9/1983 | Taaks et al. |
| 4,449,537 | A | * | 5/1984 | Pross et al. ..................... 600/536 |
| 5,305,745 | A | * | 4/1994 | Zacouto ......................... 600/324 |
| 5,445,144 | A | * | 8/1995 | Wodicka et al. .......... 128/207.14 |
| 5,653,241 | A | * | 8/1997 | Harada et al. .................. 600/493 |
| 2001/0011159 | A1 | * | 8/2001 | Cantrell et al. .................. 601/41 |
| 2002/0032383 | A1 | | 3/2002 | Bisera et al. |
| 2002/0035339 | A1 | * | 3/2002 | Kavet et al. .................... 600/547 |
| 2003/0109795 | A1 | * | 6/2003 | Webber ........................ 600/543 |

FOREIGN PATENT DOCUMENTS

| EP | 0747005 | 12/1996 |
| FR | 2652255 | 3/1991 |
| WO | WO 89/07415 | 8/1989 |

OTHER PUBLICATIONS

Mehta et al. (An assessment of the ability of impedance respirometry to distinguish oesophageal from tracheal intubation). Anaesthesia, 2002, 57, pp. 1090-1093.*

Maeda, Teaching by Certified Nurse of Intensive Care of Serious Injury, Prohibition! Administration of Artificial Breathing 50, for Adults, Fixing of Endotracheal tube, Nursing Today, Japan, Japanese Nursing Association, May 1, 2002, vol. 17-6 No. 207, p. 121-123.

* cited by examiner

Primary Examiner — Charles A Marmor, II
Assistant Examiner — Christian Jang
(74) Attorney, Agent, or Firm — Hunton & Williams LLP

(57) ABSTRACT

The invention comprises an apparatus and a method for externally assessing and monitoring placement of an endo-tracheal tube for ventilation of patients based on thoracic impedance measurement.

24 Claims, 11 Drawing Sheets

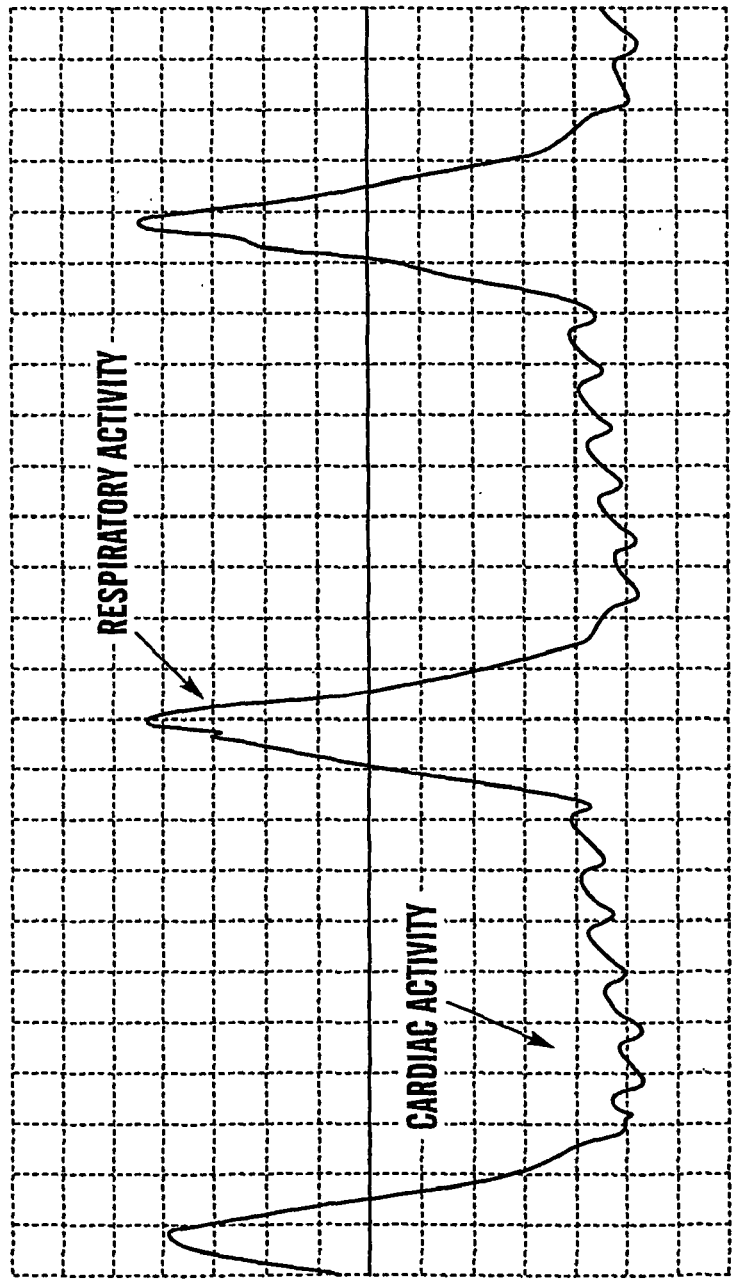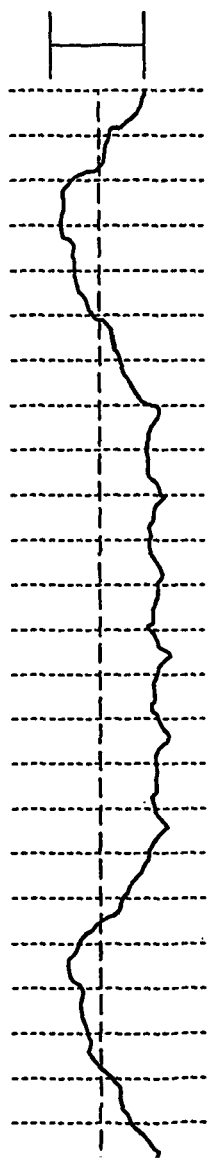

INTUBATION MONITORING APPARATUS AND METHOD

This application claims the benefit under 35 USC §119(e) to U.S. Provisionsal Application 60/390,115 filed, 21 Jun. 2002.

The present invention relates to an apparatus and a method for assessing correct endo-tracheal intubation immediately after intubation and for monitoring correct placement of the endo-tracheal tube over time.

Endo-tracheal tubes are used during general anaesthesia, intensive care, and cardiopulmonary resuscitation. The endo-tracheal tube is used to secure the airways to the patient's lungs. Insertion of an endo-tracheal tube is carried out with the aid of a laryngoscope. This device allows the operator to visually identify the larynx and pass the tube through it into the trachea. In some cases the larynx may not be seen and the chance arises of a tube being erroneously passed into the oesophagus as opposed to the trachea.

An endo-tracheal tube erroneously passed into the oesophagus does not provide an adequate airway, so that the patient may become deprived of oxygen, and serious harm or even death may result.

During transportation or moving of a patient the endo-tracheal tube may be unwontedly relocated, without any clinical signs of this condition appearing before it is too late.

Recognition of correct endotracheal intubation as soon as possible is thus of paramount importance. It is also important to be able to monitor intubation in the cases where there is a risk of unwonted relocation of the tube.

The usual method of confirming the correct location of the tube involves pumping a quantity of air or gas through the tube into the patient. With a stethoscope it is possible to hear normal ventilation sounds if the tube is placed in the trachea. However, in a stress situation and/or a noisy environment, it is difficult to hear these important ventilation sounds.

As a consequence of this, several devices which are not based on hearing ventilation sounds are introduced. These may e.g. be based on pressure and End tidal $CO_2$ measurements. End Tidal $CO_2$ measurements are based on an analysis of the patient's expiration air, if this air contains $CO_2$, it has been in the patient's lungs and the intubation is correct. However, a measurement of $CO_2$ contents depends on several parameters (blood flow through the lungs, gas exchange in the lungs, ventilation volume per ventilation, ventilation amount per minute, etc). In cases where the blood flow through the lungs is strongly reduced, and the patient ventilation is constant, the End Tidal $CO_2$ level will be almost cero. This can be wrongly interpreted as an incorrect intubation. As End Tidal $CO_2$ depends on other physiological parameters for the patient that can be failing at the time intubation is performed, it cannot be considered as a reliable method.

Other devices use the change of transthoracal diameter as a factor to detect correct intubation. Again transthoracic diameter measurement can be affected by several sources of error. Sometimes the patient's thorax is so rigid that it does not expand appreciably by inhalation. In these cases, the abdominal cavity expands as a consequence of diaphragm movement. These will of course be erroneously interpreted as the patient receiving air in the stomach (wrong intubation).

WO 89/07415 describes an apparatus for locating an endo-tracheal or endo-oesophageal tube. This apparatus comprises a tube for insertion into the trachea or oesophagus of a patient. The tube is provided at its' distal end with a pair of electrodes arranged in such manner that the impedance measured between the conductors varies depending on the probe being placed in the trachea or in the oesophagus. If the probe is in the trachea, which is a somewhat rigid tube, one of the electrodes will be in contact with the trachea while the other is not. This will lead to one impedance value. If the probe is in the oesophagus, which is a soft tube which will contract on the probe, both electrodes will touch the mucosa and a second impedance value will be read. This measuring principle is highly unreliable, as it is based on a presumption on how the patient's trachea/oesophagus will react upon placement of the probe. It will not yield reliable results for patient with non-standard configuration of the trachea or the oesophagus, or patients with injuries to these parts of the bpdy. Besides, use of this apparatus together with a common intubation probe will lead to a double intubation.

Due to the above mentioned disadvantages related to the prior art methods, there exists a need for an apparatus and a method for assessing correct positioning of an endo-tracheal tube both immediately after intubation and for monitoring its' positioning over time.

The present invention is based on impedance measurement of the thoracic cavity. This measurement is performed from the outside of the thorax. Impedance measurement involves the use of at least two electrodes which receive an approximately constant direct (or alternating) current, measurement of the direct (or alternating) voltage between the electrodes and calculation of the ratio voltage/current (impedance). In a preferred embodiment of the invention, the apparatus comprises four electrodes to avoid introducing the electrodes' impedance in the measurement; the supplied current is alternative current with a frequency range of between 50 and 100 kHz, e.g. 80 kHz.

The principle behind the invention is that transthoracal impedance of inflated lungs is different from the impedance of deflated (or empty) lungs. This is due to the presence of an insulation material (air) between electrodes when the lungs are inflated. The invention makes use of this change in impedance to distinguish between correct and incorrect intubation. When the endo-tracheal tube is placed in the trachea and the lungs are ventilated, a change in transthoracal impedance will be noticeable immediately. On the contrary, when the tube is placed in the oesophagus or stomach it will not be possible to measure any significant impedance change of the thorax.

The invention comprises thus an apparatus for immediate and continuous position monitoring of an endo-tracheal tube for ventilation of patients. The apparatus for assessing and monitoring placement of an endo-tracheal tube for ventilation of patients comprises a measuring unit with at least two measuring electrodes,
a power source for activating the measuring electrodes,
a user interface device to start/stop the monitoring,
a display or an alarm device for signalling whether the lungs are being inflated or not, and consequently whether the intubation device is correctly or incorrectly positioned, and
a connection unit for transmitting signals between the electrodes, the power source, the user interface device and the display device. The apparatus is characterised in that the electrodes are adapted for placement on the thoracic cavity so as to measure the thoracic impedance externally.

The apparatus according to the invention permits to assess correct intubation swiftly and reliably without subjecting the patient to unnecessary stress. It can be used in injured patients, in patients that are not breathing, in cases where there is PEA, and also together with defibrillation devices.

The apparatus according to the invention can be used together with any intubation devices and this provides high flexibility.

In a preferred embodiment of the invention the measuring unit comprises four electrodes, two electrodes adapted to apply current to the thoracic cavity and two electrodes adapted to measure voltage drop across the thoracic cavity.

In a further preferred embodiment of the invention the connection unit comprises a processing unit for: receiving a start command from a user interface device, controlling the measurement process, calculating and analysing impedance signals, identifying significant impedance changes over time, and transmitting a signal representative of "ventilation" or "no ventilation" to a display or an alarm device, and a memory unit for storage of measured, calculated and reference values.

The invention comprises also a method for assessing and monitoring placement of an endo-tracheal tube for ventilation of patients, where a) thoracic impedance signals are obtained based on measurement data obtained from a measuring unit, and characterised by, b) analysing the impedance signals to identify changes in impedance over time,
c) comparing the impedance changes to a predetermined threshold value, and
d) activating a first display or alarm device if the changes' magnitude does exceed the predetermined value to signalise correct intubation and/or activating a second display or alarm device different from the first device if the changes' magnitude does not exceed the predetermined value to indicate incorrect intubation.

In an advantageous embodiment of the method according to the invention, steps a)-c) are performed at a processing unit connected to the measuring unit, and the threshold value is stored in a storage unit connected to the processing unit. In a further variant of this embodiment, previous to steps a) a start signal is given to the processing unit by a user, and steps a)-d) are repeated a during a predetermined period of time or until a stop signal is given to the processing unit by a user It is important to point out that the apparatus according to the invention only has a low power consumption, since it only requires power for impedance measuring devices, processing/memory devices and alarm devices. This clearly distinguishes the invention from defibrillator devices, which require high power when operated to give shock. Since the power needs of the apparatus according to the invention are low, it is possible in one embodiment, to provide an apparatus where the power source comprises low energy, small portable batteries.

The measurement electrodes in the apparatus according to the invention are adapted to provide high sensibility. They are adapted to contact the skin with lowest possible losses. The electrodes have as a main function to facilitate the transition between current conduction in the electrode (electrons) and in tissue (ions).

In a simplified version, the apparatus comprises an activating switch (user interface device), two electrodes and a light emitting device. When the electrodes are in place on the patient's chest, the apparatus is turned on. The patient's impedance is measured and as soon as a change in impedance which exceeds a predetermined threshold is detected the light emitting device is turned on. The light emitting device will be activated as long as the impedance value lies over the threshold and will be turned off automatically when the impedance decreases below it. This embodiment permits a continuous monitoring of the intubation. If a change of impedance exceeding the threshold is not detected, a second alarm or display device is activated to signalise incorrect intubation.

It is possible to provide the device with a switch having three positions: off, single measurement, monitoring. In the "off" position impedance, detection is not performed. In the "single measurement" position, the apparatus measures the impedance value a predetermined number of times or during a predetermined period of time before it stops. This operation modus will be useful for monitoring adult patients because once the intubation is correct the chances of the tube coming out of place are low. In the "monitoring" position, the measurements will be performed continuously until the apparatus is turned off. This operation modus is useful for monitoring of small children and also for monitoring patients in turbulent conditions (in a helicopter, a boat, mountain rescue, etc). In the "monitoring" position, it is also possible to measure and analyze the patient's breathing rate, and to activate a further alarm device if this rate does not lie within a predetermined range.

It is also possible to supply the apparatus with several light/sound emitting or display devices. This will help avoid the situation where no alarm is activated due to failure of the equipment. As mentioned before a preferred embodiment of the invention will then have a first signal output indicating that there is ventilation of the lungs and a second signal output indicating absence of ventilation. This second signal output will be activated after a predetermined period of time (e.g. 5 seconds) without an impedance change being detected.

In one embodiment of the invention, the apparatus comprises a device for controlling the batteries' charge condition and a device for checking correct functioning of the alarm devices (light/sound emitting devices). This device comprises in one embodiment a display showing battery charge condition and e.g. a button that upon pressure forces a connection of the light/sound device to the battery so that said device is activated.

The apparatus can also comprise devices for control of the electrodes.

The user interface device can also in one embodiment of the invention permit inputting reference and threshold values for thoracic impedance to the processing units. It can also permit inputting patient characteristics, as e.g. patient age or choosing between patient groups to specify which group the patient belongs to.

Although the apparatus according to the invention is in one embodiment envisaged as an independent portable apparatus, it is also possible to incorporate it in defibrillators or other devices used in resuscitation/monitoring procedures (e.g. ECG devices). A device comprising an ECG apparatus and the apparatus according to the invention will permit detection of Pulseless Electrical Activity (PEA), that is, a condition where the heart sends electrical signals but the patient does not breathe.

As soon as the pads or electrodes are placed on the thorax the apparatus will measure the unique impedance for that patient at "resting" level, this value will be stored together with a time reference for later use. It is documented that each thorax has its unique impedance. When the amount of air or blood in the thorax is changed either by ventilation or by blood flow or by chest compressions (in cardiac arrest) the thoracal impedance will change. A new measurement and a comparison with the stored value will result in a significant difference in impedance values if the lungs are inflated. Only one ventilation is then needed to measure impedance change due to an air volume change of the thorax.

The invention will now be explained in further details by means of non limiting examples illustrated in the attached drawings, where:

FIG. 3 shows a diagram of thoracic impedance vs. time.

Figure 1:
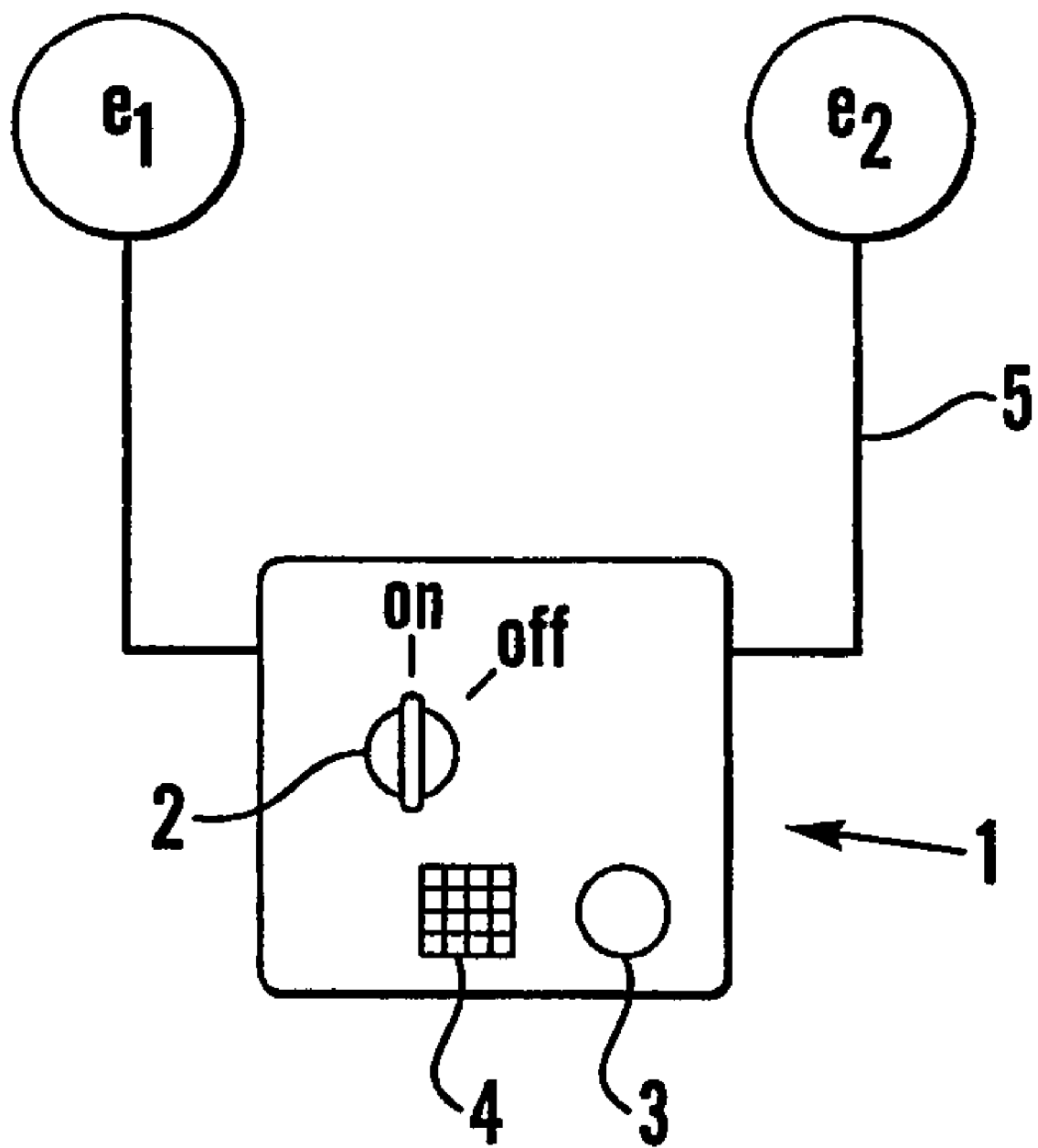
FIG. 1 is a view of an embodiment of the apparatus according to the invention.

FIG. 1 shows an embodiment of the apparatus according to the invention. The apparatus comprises a housing 1 containing a user interface device 2, which in this case is a revolving switch with "on" and "off" positions. The housing contains also a power source (not shown) in the form of portable batteries, a light emitting device 3 and a sound emitting device 4. Electrodes e1 and e2 are connected to the housing by means of cables 5. In this embodiment of the invention, the light and sound emitting devices (3 and 4 respectively) will be activated if a significant change in thoracic impedance is detected after a preset time period. It is possible to envisage an embodiment comprising several light/sound emitting devices or a display device that are activated selectively according to the magnitude of the thoracic impedance changes.

In a preferred embodiment of the invention which will be described in detail later, the measuring unit comprises four electrodes, two electrodes to apply a current to the thoracic cavity and two to pick up a voltage signal. It is possible to position one current electrode and one voltage electrode in the same pad so that only two pads are placed on the patient's thorax.

The term "impedance" refers generally to a complex value comprising a resistive and an inductive/capacitive part, but it is clearly possible to implement the invention by measuring only the resistive/capacitive and/or inductive part of the impedance. The measurements can be performed by means of AC or DC voltage/current. In the DC case, only the resistive part of the impedance will be measured. However, use of DC for measurement will be inappropriate because the body tissue is capacitive. A DC measurement will then just reflect the resistance of the skin layer. Because of this, in a preferred embodiment of the invention AC voltage/current is used.

It will be evident that measurement of voltage/current/conductance may be employed in an equivalent way for determining the thoracic impedance.

Figure 2:
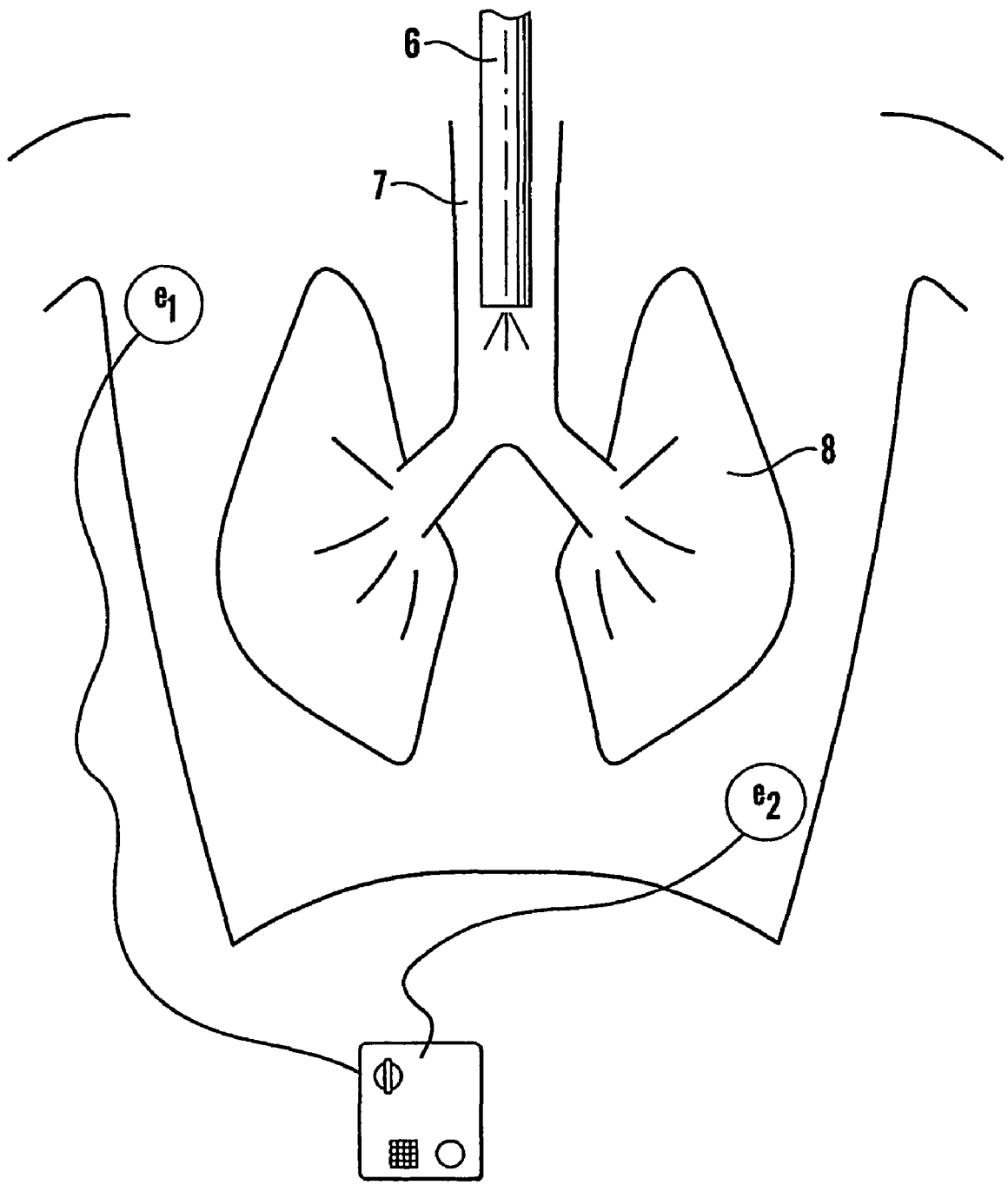
FIG. 2 shows an endotracheal tube and the apparatus according to the invention on a patient.

FIG. 2 shows how the apparatus 1 according to the invention will cooperate with an endotracheal tube 6. If the tube 6 is positioned correctly, the trachea 7 will transmit a flow of air to the lungs 8, these will inflate and an impedance value will be measured by means of electrodes e1 and e2 (or e1, e2, e3 and e4). If this value represents a significant increase in thoracic impedance, the intubation will be correct and the first light/sound emitting devices will be activated. If said value on the contrary does not represent a significant increase in thoracic impedance, the first light/sound devices will not be activated. Optional light/sound emitting devices will be activated if the threshold is not exceeded.

FIG. 3A shows a diagram of thoracic impedance vs. time for a breathing patient. From the diagram it is clear that the respiratory activity causes considerable changes in transthoracal impedance. This is also shown in tests performed by means of the invention as will be explained later. The respiratory impedance will have a variation of $0.5\Omega$ between peak and valley (FIG. 3B). These diagrams can be found in the article "Expanding Automatic external defibrillators to include automated detection of cardiac, respiratory, and cardiorespiratory arrest" by Tommasso Pellis, Joe Bisera; Wanchung Tang, and Max Harry Weil, Crit Care Med 2002, Vol. 30, Nr 4 which is included as a reference.

Figure 4:
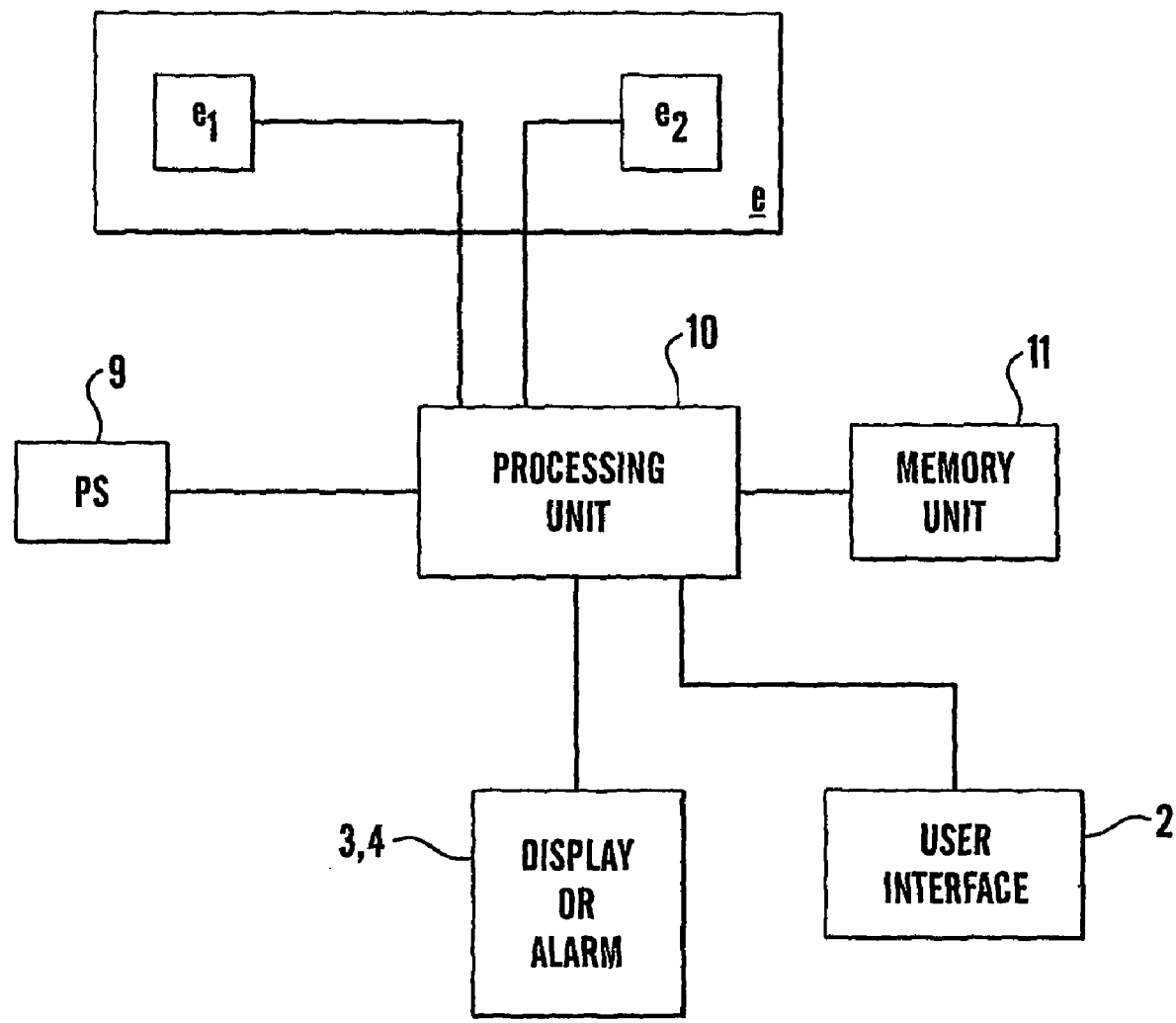
FIG. 4 is a block diagram of an embodiment of the apparatus according to the invention.

FIG. 4 shows a block diagram of an embodiment of the apparatus according to the invention. The figure shows measuring unit e comprising electrodes e1 and e2 adapted for measurement of thoracic impedance, a power source 9 for activating the measuring unit e, a user interface device 2 to start/stop the monitoring, a processing unit 10 for: receiving a start command from user interface device 2, controlling the measurement process, calculating and analysing impedance signals, identifying significant impedance changes over time, and transmitting a signal representative of "ventilation" or "no ventilation" to the display or an alarm device 3, 4, a memory unit 11 for storage of measured, calculated and reference values.

Figure 5:
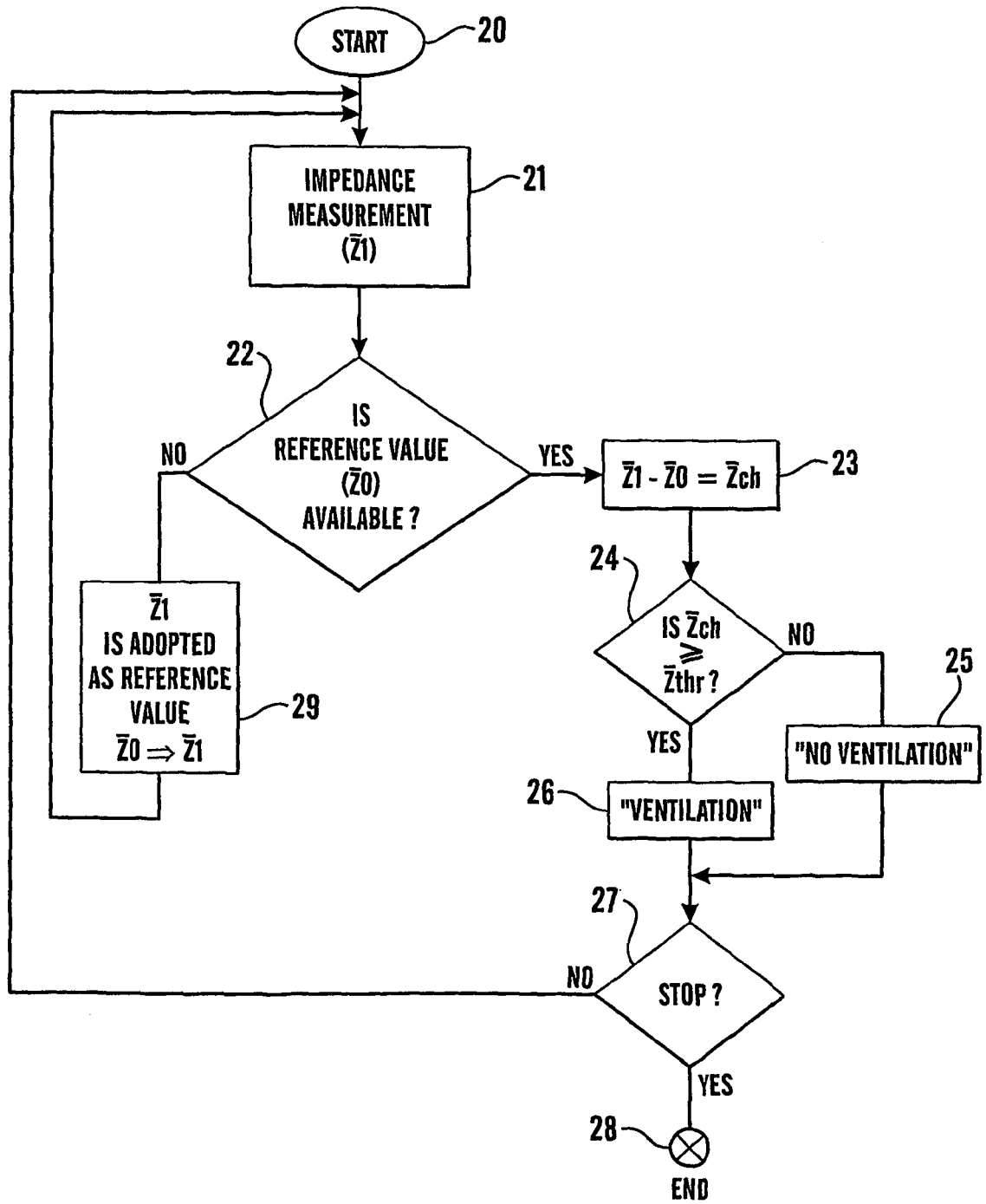
FIG. 5 shows a diagram of one embodiment of the invention.

FIG. 5 shows a diagram representing one embodiment of the method according to the invention. In step 20 a start command is transmitted from the user interface device 2 to the processing unit 10. In step 21 an impedance (Z1) measurement is performed by means of measuring unit e and processing unit 10. In order to establish a change in impedance value, a reference value (Z0) must be supplied to the processing unit 10. Availability of the reference value Z0 is controlled (Z0 can be at the storage or memory unit 11 or can be inputted by means of the user interface device 2) in step 22. If Z0 is available, an impedance change (Zch) is calculated by means of the processing unit 10 in step 23 and this change is compared with a threshold value (Zthr) in step 24. The threshold value Zthr must also be available in the storage or memory unit 11, or provided by means of the user interface device 2. If the threshold value is not reached (step 25) a "no ventilation" condition will be assessed and the corresponding alarm units 3, 4 will be activated by means of the processing unit 2. In this embodiment of the invention the measurement/comparison/alarm activating process will continue as long as a stop signal is not given by the user interface device 2. If the apparatus is turned off (step 28) the process will end. If the threshold value is reached or exceeded (step 26) a "ventilation" condition will be confirmed and the corresponding alarm units will be activated.

If a reference value Z0 is not available, the result of the first measurement or a magnitude derivated from earlier measurements will constitute a new Z0 (step 29), and the process will continue as stated before in relation to steps 21 to 28.

The memory or storage unit 11 further comprises a memory portion containing executable computer program instructions for performing the method according to the invention when executed by the processing unit 10.

The implementation of these executable instructions is an ordinary task for a person skilled in the art, based on the disclosure of the invention.

FIG. 5 shows one possible embodiment of the method, but other variants are also possible. The reference value Z0 and the threshold value Zthr can be stored in a table according to the patient's characteristics (sex, age, weigth, etc.). The user interface device can have a further switch to chose between patient groups and thus establish the current Z0 and Zthr values.

Figure 6:
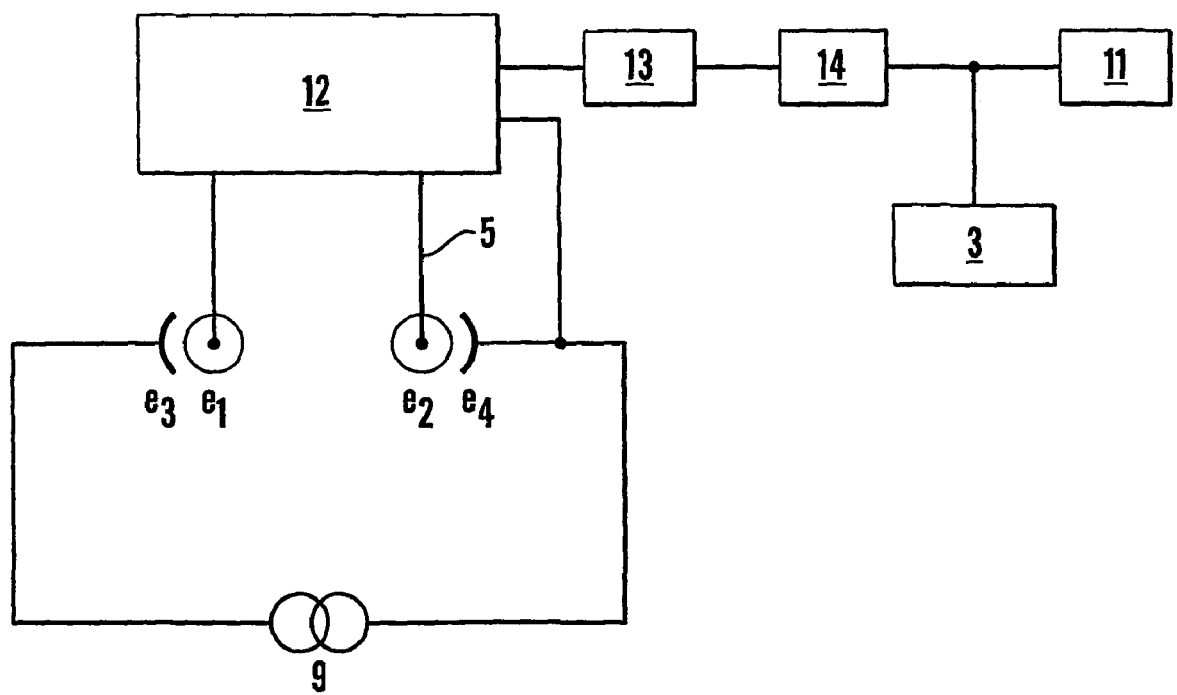
FIGS. 6-9 show an embodiment of the measuring unit according to the invention.

FIG. 6 shows a diagram of the measuring unit e in one embodiment of the invention. The measuring unit comprises:
  a power supply source which energises the different components, this source is shown in further detail in FIG. 7,
  a "current carrying circuit" that feeds the electrodes e3 e4 for applying a current to the thorax, the current is supplied by a current source 9, and has a magnitude of 500 μA and a frequency of 80 Hz, this circuit is shown in further detail in FIG. 8, a "pick up" circuit or detecting circuit comprising electrodes e1 and e2, an instrument amplifier 12 for measuring/amplifying difference signals, a low pass filter 13 (to filtrate DC before rectification, since only the AC component of the signal is of interest) and a precision rectifier 14 to provide a DC output, this circuit is shown in further detail in FIG. 9.

Figure 7:
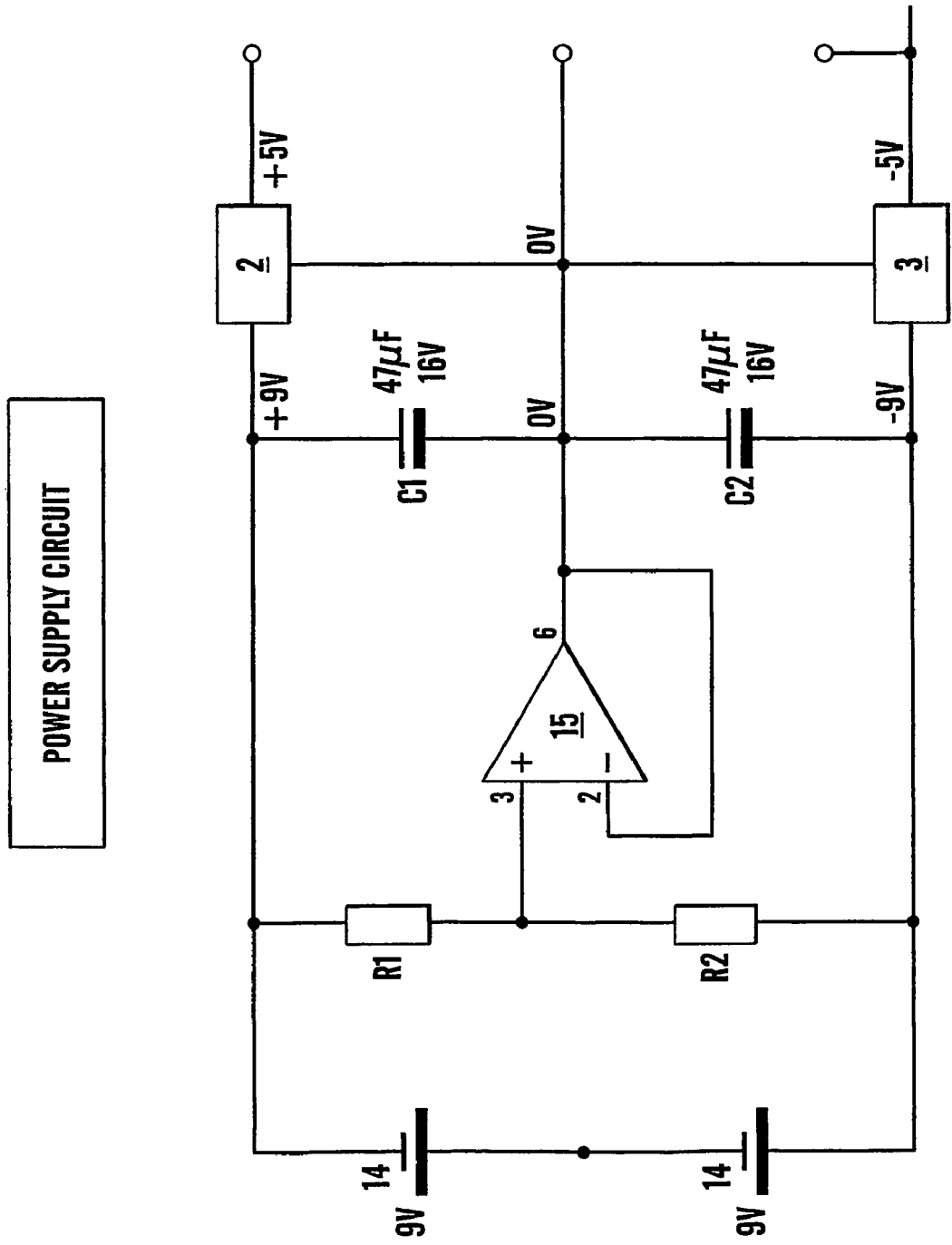

FIG. 7 shows the power supply for the components. This comprises two DC 9V batteries 14, two resistances R1 and R2, an amplifier 15 implemented as an IC of type LM74/CN, two 16V, 47 μF capacitors C1 and C1, two IC type L7805 and L7905.

Figure 8:
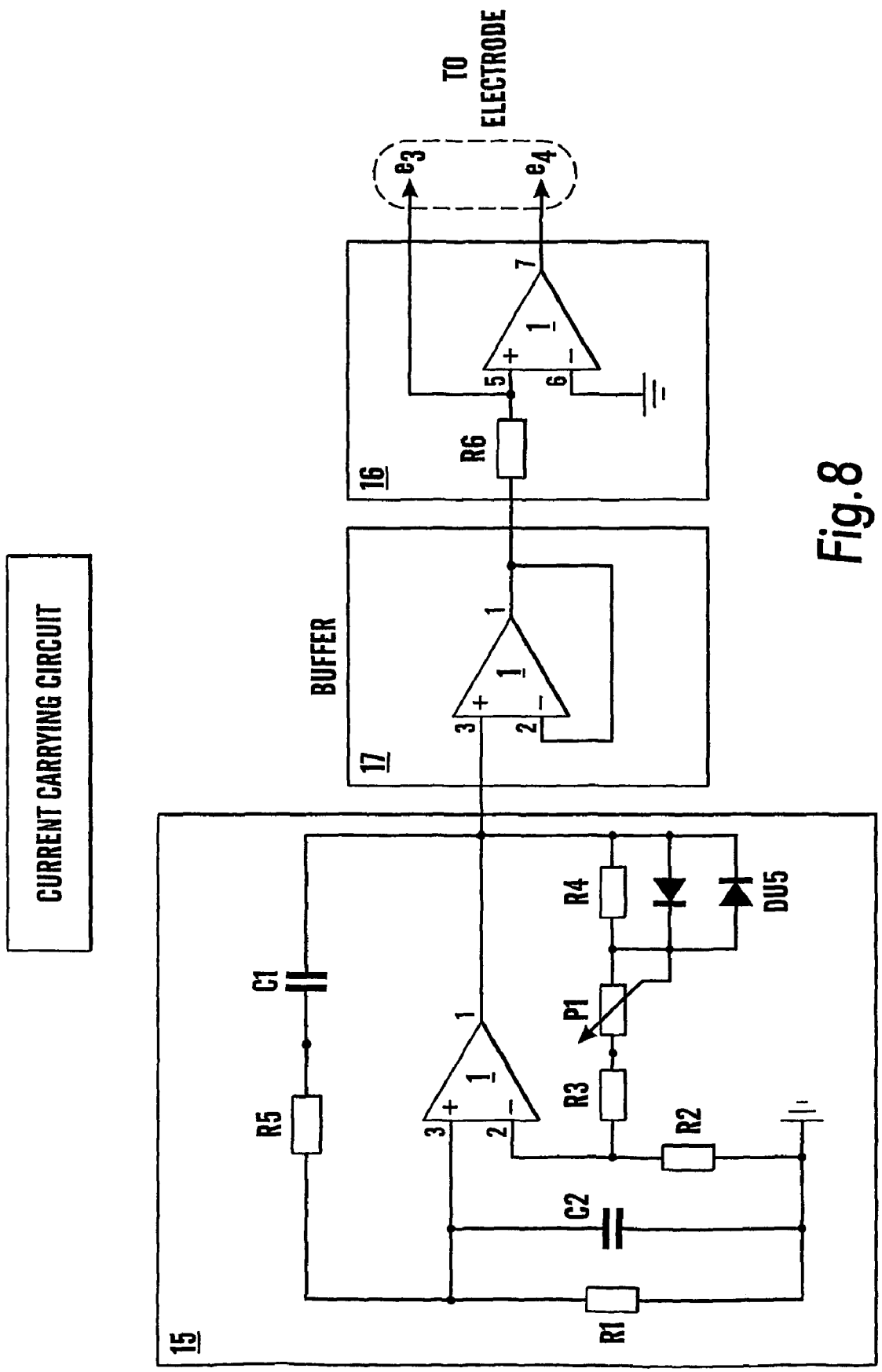

FIG. 8 shows the current carrying circuit. This circuit comprises a sinus oscillator 15, a constant current generator 16, and a buffer circuit 17 on the output.

Figure 9:
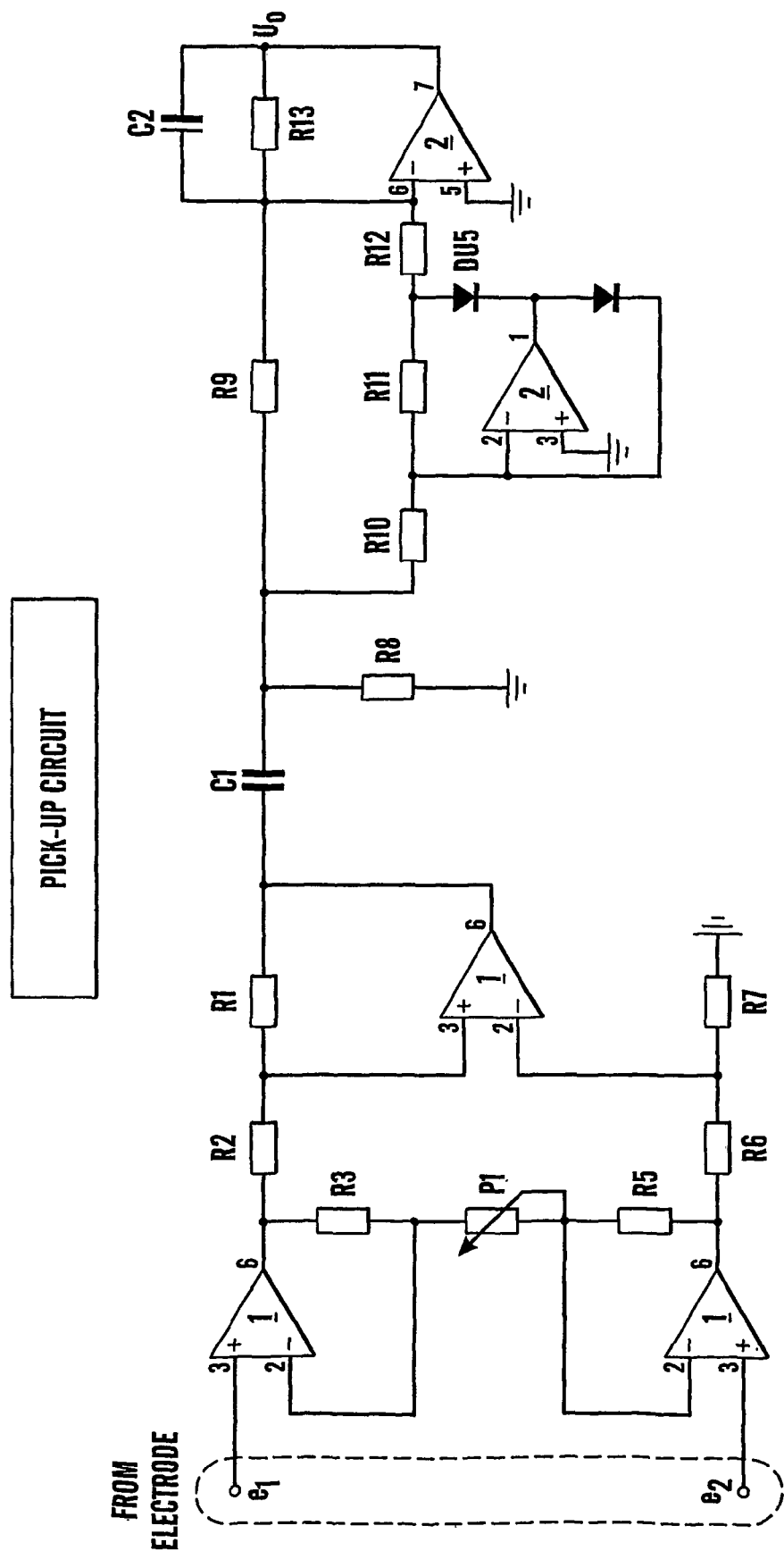

FIG. 9 shows the pick up circuit.

When the apparatus is connected to the thorax, a current is sent through the current electrodes e3 and e4 which are connected to the currant carrying circuit. The other two electrodes e1 and e2 which are connected to the pick up circuit will register the voltage drop across the thorax. This voltage drop is sent to a processing unit which as mentioned before controls display and alarm devices.

The measuring unit shown in FIGS. 6-9 was used to test the method according to the invention on a pig.

The pig was placed supine on an operating table and anesthetized. A first endotracheal tube was placed in the trachea. During preparation the pig was ventilated through this tube (tube 1). A second tube (tube 2) was placed through the oesophagus in order to ventilate the stomach (incorrect intubation). Electrodes e1, e2, e3, e4 were attached to the pig's chest at four different places and these were connected to the measuring unit. The output of the measuring unit was connected to an oscilloscope.

Figure 10:
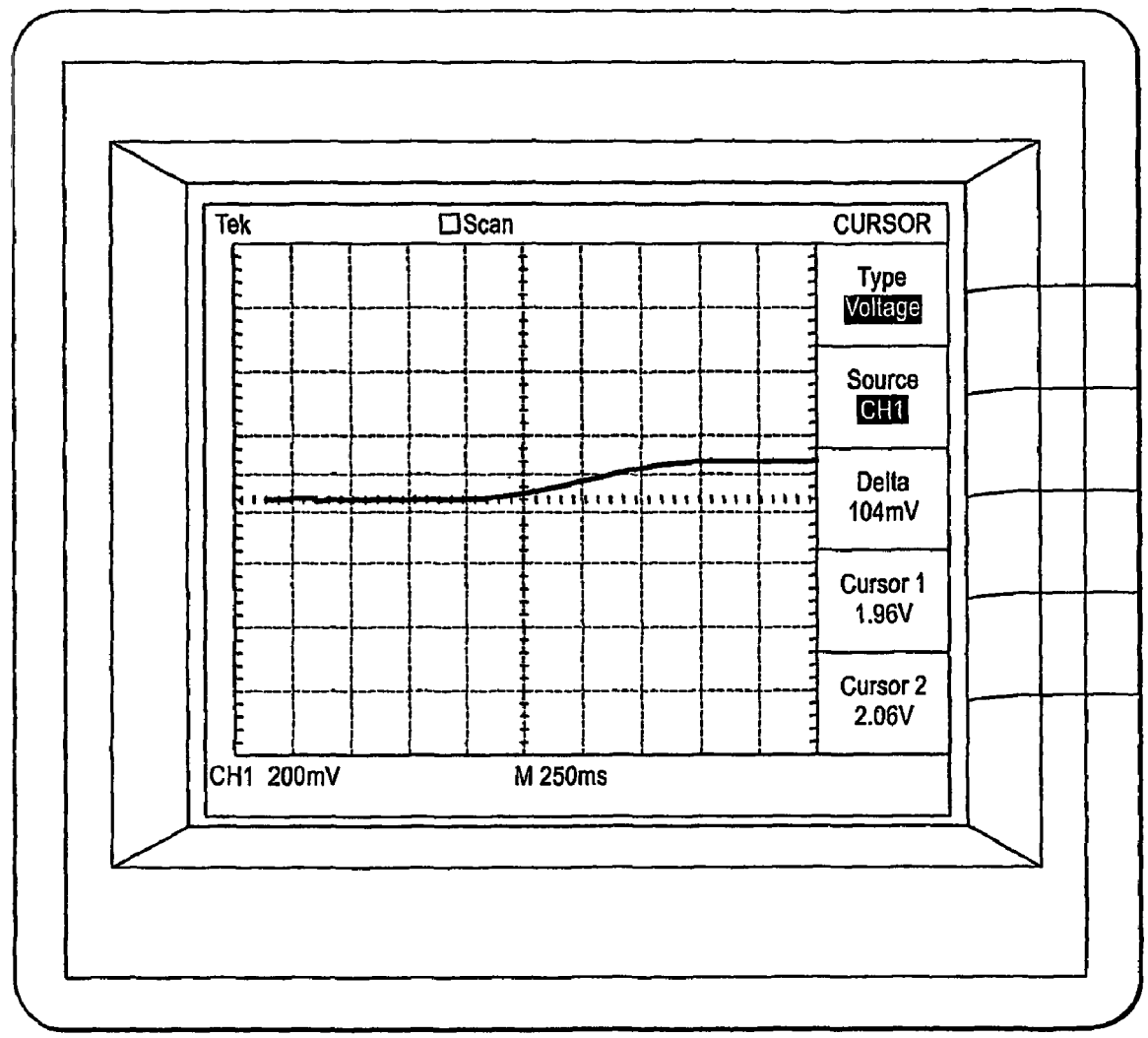
FIGS. 10 and 11 show results of a test performed by means of the measuring unit in FIGS. 5-8.

During ventilation of the lungs through tube 1 fluctuations were observed in the oscilloscope's output, these fluctuations correspond to impedance changes and are shown in FIG. 10. The fluctuations were in the order of magnitude of 10 mV.

Figure 11:
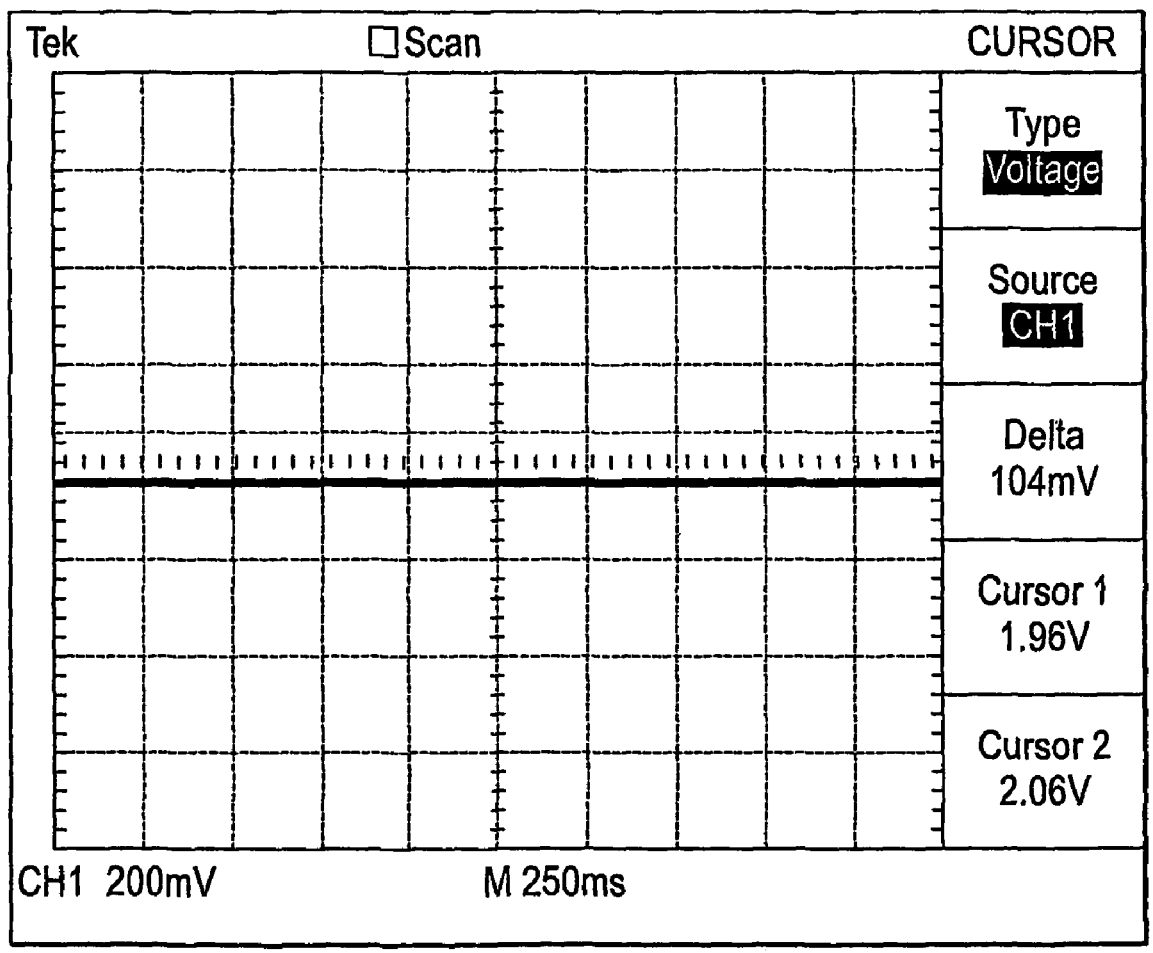

The ventilation bag was then connected to tube 2 and "ventilation" attempts were performed. Measurements of impedance changes were performed, and no fluctuation was detected. The results are shown in FIG. 11.

The output signal of the apparatus according to the invention (light/sound/image) for monitoring intubation will not be influenced by ambient noise (as opposed to the prior art stethoscope technique, it being difficult to hear lung sounds with a stethoscope), low cardiac output (which will influence ET $CO_2$ measurements), and does not imply the delay of several ventilation attempts before satisfied.

The apparatus can be used for monitoring adults, children, and newborns. As stated before, it may be used as an alarm device during intensive care and transportation of all age groups of patients, in order to monitor correct placement of the tube.

The invention comprises also a method for immediate detection of correct/incorrect intubation, that is, instant detection of correct/incorrect placement of the tube during intensive care and transportation of intubated patients.

The invention claimed is:

1. An apparatus capable of detecting either or both of that an endo-tracheal tube for ventilation is placed correctly in a recipient or alternatively that an endo tracheal tube for ventilation is placed incorrectly in a recipient, the apparatus comprising the following elements:
    (i) a processing unit for detecting impedance amplitude changes;
    (ii) a measuring unit comprising at least two measuring electrodes for measuring the impedance of a body, the measuring unit being in communication with the processing unit;
    (iii) a power source for the apparatus; and
    (iv) a display or alarm device;
    wherein, in use, a correct placement of the endo-tracheal tube in a recipient upon ventilation is indicated by the processing unit by detecting a significant change in the impedance amplitude and the incorrect placement of the endo-tracheal tube in a recipient upon ventilation is indicated by the processing unit by detecting a change in the impedance amplitude that is below a specified threshold level, and further wherein during use of said apparatus the change in the impedance amplitude is shown on the display or is indicated by the activation of the alarm.

2. The apparatus as claimed in claim 1 wherein, in use, a correct placement of the endo-tracheal tube is indicated by the processing unit identifying a significant change in the impedance amplitude above a specified threshold level and/or an incorrect placement of the endo-tracheal tube is indicated by the processing unit)by identifying a change in the impedance amplitude below the said specified threshold level, and the change in the impedance amplitude is shown on the display or is indicated by the activation of the alarm.

3. An apparatus as claimed in claim 1 or claim 2 wherein, the specified threshold level is an impedance amplitude of 0.5 ohms.

4. An apparatus programmed to indicate the placement of an endo-tracheal tube for ventilation, the apparatus comprising the following elements:
    a processing unit for identifying impedance changes upon ventilation;
    a measuring unit comprising at least two measuring electrodes for measuring the impedance of a body, the measuring unit being in communication with the processing unit;
    a power source for the apparatus; and
    a display or alarm device,
    wherein the processing unit is programmed to identify impedance changes above a specific threshold value, and wherein the processing unit is programmed to receive an impedance measurement value, and to identify if the impedance value is equal or greater than the specific threshold value, and further is programmed such that if the specified threshold value is not reached then the processing unit will activate either or both the alarm device and or the display device thereby indicating incorrect intubation of an endo tracheal tube in a recipient.

5. An apparatus as claimed in claim 4 wherein the processing unit comprises a memory unit for the storage of measured, calculated and threshold values.

6. An apparatus as claimed in claim 4 wherein the processing unit comprises an "on/off" switch or a three position switch comprising a first "off" position, a second "single measurement" position, and a third "monitoring" position.

7. An apparatus as claimed in claim 4 wherein the specified threshold value is 0.5 ohms.

8. An apparatus as claimed in claim 4 wherein the processing unit operations are repeated over a period of time in order to monitor the placement of the endo-tracheal tube for ventilation.

9. An apparatus as claimed in claim 4, wherein the alarm device comprises at least one of a sound emitting device and a light emitting device.

10. An apparatus as claimed in claim 4 wherein the apparatus further comprises a user interface is adapted for inputting reference thoracic impedance values, threshold impedance values, and/or patient characteristics to the processing unit.

11. An apparatus as claimed in claim 4, wherein the apparatus is adapted for integration in a defibrillating device.

12. An apparatus as claimed claim 4 wherein the apparatus further comprises an endo-tracheal tube for ventilation.

13. An apparatus programmed to indicate the placement of an endo-tracheal tube for ventilation, the apparatus comprising the following elements:
  a processing unit for identifying impedance changes upon ventilation;
  a measuring unit comprising at least two measuring electrodes for measuring the impedance of a body, the measuring unit being in communication with the processing unit;
  a power source for the apparatus; and
  a display or alarm device,
  wherein the processing unit is programmed to identify impedance changes above a specific threshold value, and wherein the processing unit is programmed to carry out the following steps:
  receive a first impedance measurement value,
  identify if there is a threshold value, if there is no threshold value adopt the first impedance measurement value as the threshold value,
  receive a second impedance measurement value and then identify if the impedance value is equal to or greater than the specified threshold level, if the threshold value is not reached then the processing unit will activate at least one of the alarm device and the display device to indicate incorrect intubation.

14. An apparatus for detecting the placement of an intubation tube in a recipient, the apparatus comprising:
  a source for providing a threshold value of thoracic impedance for said patient
  a measuring unit comprising at least two electrodes, for measuring a thoracic impedance of said patient
  a display for displaying said threshold value and the measured thoracic impedance;
  wherein an indication of placement of an intubation tube is shown on said display as a change in said measured thoracic impedance as compared to said specified threshold value.

15. The apparatus of claim 14, wherein an increase in measured thoracic impedance as compared to the threshold value indicates a correct placement of the intubation tube in a recipient.

16. The apparatus of claim 14, wherein an decrease in measured thoracic impedance as compared to a specified threshold value indicates an incorrect placement of the intubation tube in a recipient.

17. The apparatus of claim 14, wherein no change in measured thoracic impedance as compared to a specified threshold value indicates an incorrect placement of the intubation tube in a recipient.

18. The apparatus of claim 14, wherein no change in measured thoracic impedance as compared to a specified threshold value indicates an correct placement of the intubation tube in a recipient.

19. The apparatus of claim 14, wherein said source is a memory unit.

20. The apparatus of claim 14, wherein said source is an input into a user interface.

21. The apparatus of claim 14, wherein said threshold value is a measured value.

22. The apparatus of claim 14, wherein said threshold value is a calculated value.

23. The apparatus of claim 14, wherein said threshold value is a reference value.

24. The apparatus of claim 14, wherein the apparatus further includes an endo-tracheal tube.

* * * * *